(12) United States Patent
Merriam et al.

(10) Patent No.: US 8,672,841 B2
(45) Date of Patent: Mar. 18, 2014

(54) DEVICE FOR USE IN A SURGICAL PROCEDURE ON A HUMAN EYE

(75) Inventors: John C. Merriam, Tenafly, NJ (US); Lei Zheng, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 12/513,195

(22) PCT Filed: Nov. 5, 2007

(86) PCT No.: PCT/US2007/023269
§ 371 (c)(1),
(2), (4) Date: May 29, 2009

(87) PCT Pub. No.: WO2008/057484
PCT Pub. Date: May 15, 2008

(65) Prior Publication Data
US 2010/0076270 A1   Mar. 25, 2010

Related U.S. Application Data

(60) Provisional application No. 60/856,681, filed on Nov. 3, 2006, provisional application No. 60/898,536, filed on Jan. 31, 2007, provisional application No. 60/927,627, filed on May 4, 2007.

(51) Int. Cl.
*A61B 1/32* (2006.01)

(52) U.S. Cl.
USPC .......................................... 600/236

(58) Field of Classification Search
USPC ................................ 600/184–246
See application file for complete search history.

(56) References Cited

U.S. PATENT DOCUMENTS

| | | | | |
|---|---|---|---|---|
| 4,428,746 A | * | 1/1984 | Mendez | 604/8 |
| 5,147,369 A | * | 9/1992 | Wagner | 606/107 |
| 5,154,283 A | * | 10/1992 | Brown | 206/63.3 |
| 5,174,279 A | * | 12/1992 | Cobo et al. | 600/206 |

(Continued)

FOREIGN PATENT DOCUMENTS

WO    WO 99/42036    8/1999

OTHER PUBLICATIONS

International Preliminary Report on Patentability ("IPRP") dated May 14, 2009, The Trustees of Columbia University in the City of New York et al.

(Continued)

*Primary Examiner* — Jan Christopher Merene
(74) *Attorney, Agent, or Firm* — Cozen O'Connor

(57) ABSTRACT

Presented is a device for use in a surgical procedure on an eye. The device includes an elongated member that includes a first elongated portion, a second elongated portion, and hook portion. The first elongated portion includes a proximal end and a distal end. The second elongated portion includes a proximal end and a distal end. The proximal end of the second elongated portion is coupled to the distal end of the first elongated portion. The second elongated portion extends from the first elongated portion at an angle to the longitudinal axis of the first elongated portion. The hook portion includes a proximal end and a distal end. The proximal end of the hook portion is coupled to the distal end of the second elongated member.

23 Claims, 7 Drawing Sheets

(56) References Cited

U.S. PATENT DOCUMENTS

| | | | |
|---|---|---|---|
| 5,451,230 A * | 9/1995 | Steinert | 606/107 |
| 5,514,076 A | 5/1996 | Ley | |
| 5,716,328 A * | 2/1998 | Grieshaber et al. | 600/206 |
| 5,807,244 A | 9/1998 | Barot | |
| 6,183,480 B1 | 2/2001 | Mackool | |
| 6,332,866 B1 | 12/2001 | Grieshaber et al. | |
| 6,620,098 B1 * | 9/2003 | Milverton | 600/236 |
| 2004/0097831 A1 * | 5/2004 | Bourne et al. | 600/564 |
| 2004/0230203 A1 * | 11/2004 | Yaguchi | 606/107 |

OTHER PUBLICATIONS

Product information for Mackool Cataract Support System, [online], [retrieved on Oct. 25, 2011], (5pp.) Retrieved from website of Impex Surgical, Inc. using internet <URL: http:/www.impexsurgical.com/>.

* cited by examiner

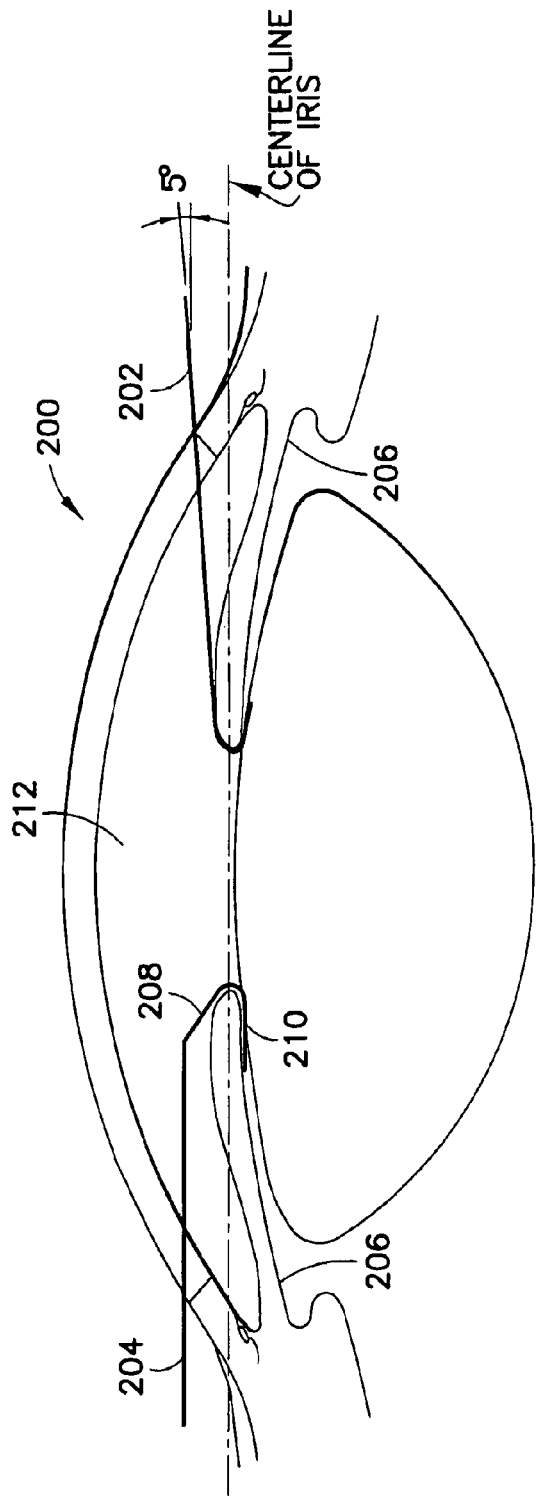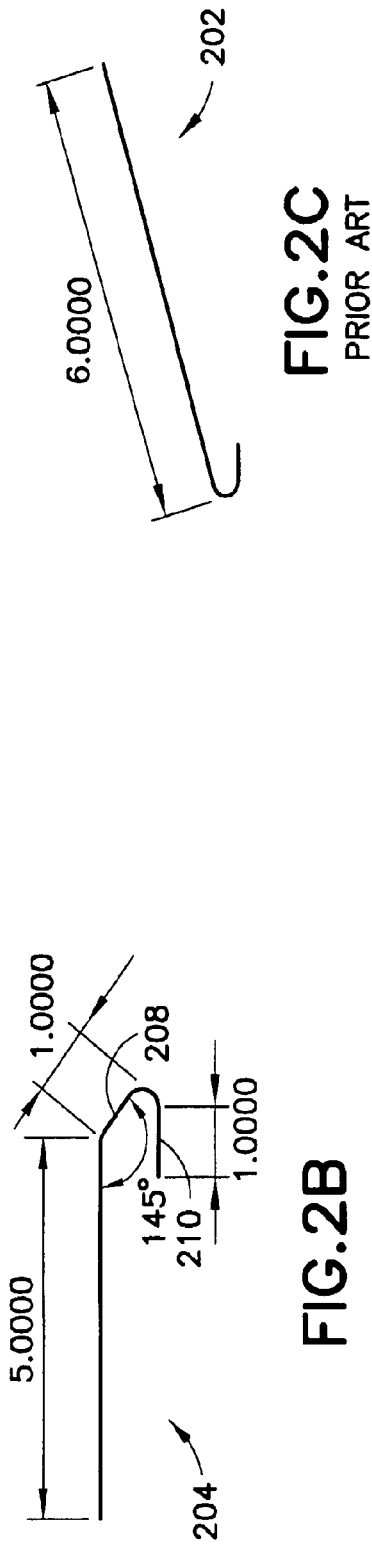
FIG. 2A
FIG. 2B
FIG. 2C
PRIOR ART

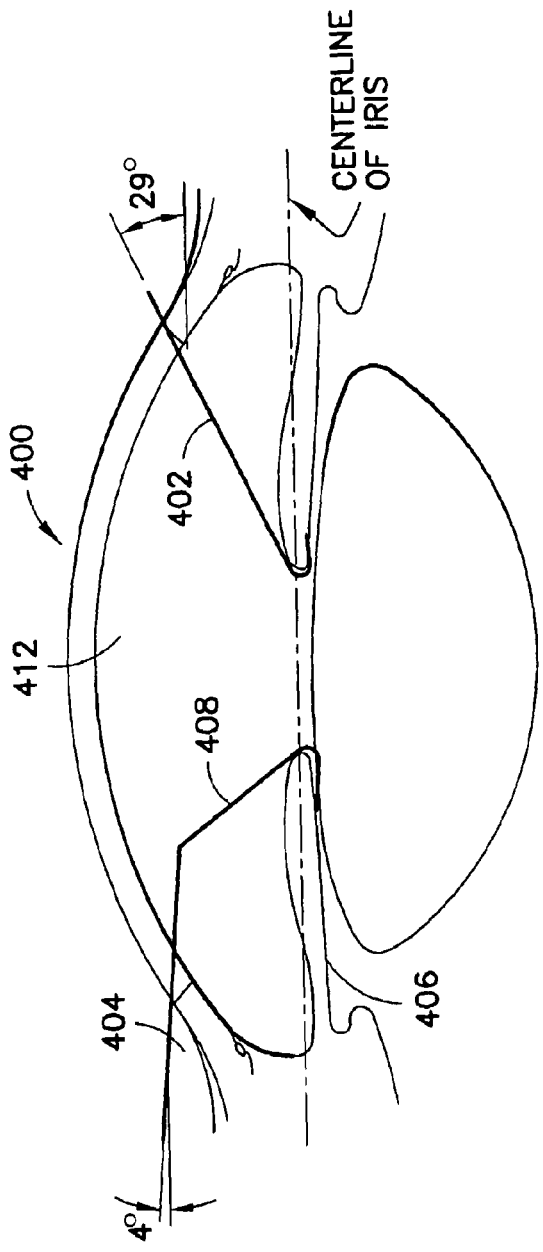
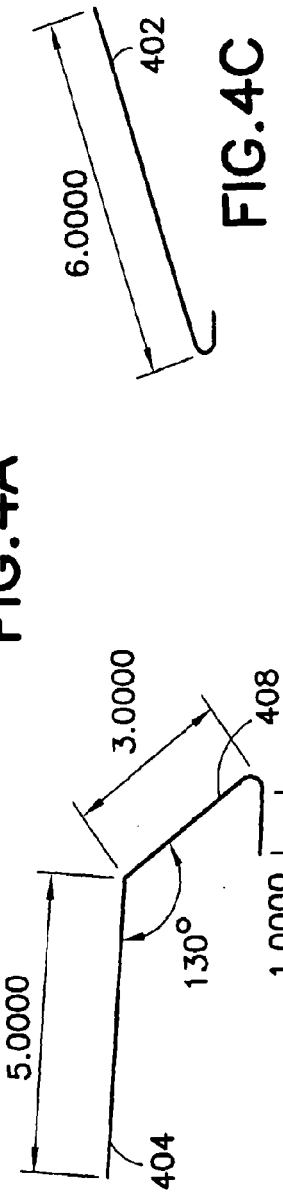
FIG.4A
FIG.4B
FIG.4C

FIG.6A
FIG.7A
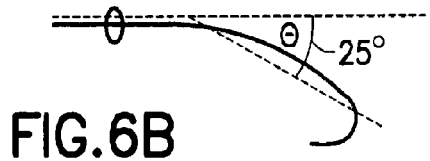
FIG.6B
FIG.7B
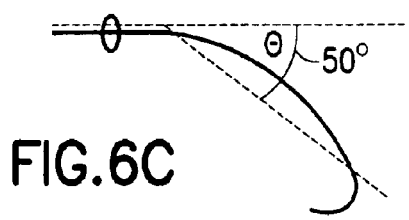
FIG.6C
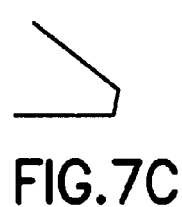
FIG.7C
 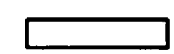  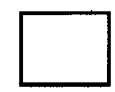 
FIG.8A  FIG.8B  FIG.8C  FIG.8D  FIG.8E
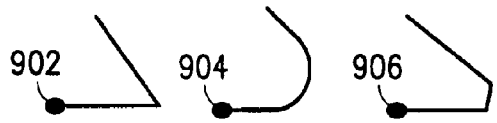
FIG.9A  FIG.9B  FIG.9C
FIG.9D  FIG.9E  FIG.9F
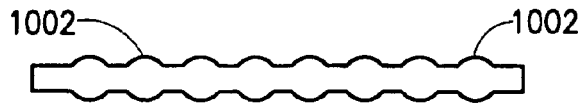
FIG.10

DEVICE FOR USE IN A SURGICAL PROCEDURE ON A HUMAN EYE

PRIORITY CLAIM

This is a U.S. national stage of application No. PCT/US07/023269, filed on Nov. 5, 2007. Priority is claimed on the following application(s): Country: U.S., Application No.: 60/856,681, Filed: Nov. 3, 2006; Country: U.S., Application No.: 60/898,536, Filed: Jan. 31, 2007; Country: U.S., Application No.: 60/927,627, Filed: May 4, 2007, the content of which is incorporated here by reference.

FIELD

The disclosed subject matter relates to bent and flexible iris retraction hooks for use in a surgical procedure on an eye.

BACKGROUND

The iris and lens undergo deformations and stress during eye surgery. In particular, the iris undergoes deformations and stress in mechanical dilation and the lens capsule undergoes deformations and stress during stabilization due to zonular degeneracy. The use of flexible nylon hooks during cataract surgery to provide mechanical dilation contributes to such deformations and stress, and can be a source of injury.

SUMMARY

In one aspect, the disclosed subject matter relates to a device for use in a surgical procedure on an eye. The device includes an elongated member. The elongated member includes a first elongated portion that includes a proximal end and a distal end, a second elongated portion that includes a proximal end and a distal end, and a hook portion that includes a proximal end and a distal end.

The proximal end of the second elongated portion is coupled to the distal end of the first elongated portion. The second elongated portion extends from the first elongated portion at an angle to the longitudinal axis of the first elongated portion. The proximal end of the hook portion is coupled to the distal end of the second elongated member.

In one embodiment, the second elongated portion is straight. In another embodiment, the second elongated portion is curved. In yet another embodiment, the hook is curved. In other embodiments, the hook is bent at an acute angle, or the hook is bent at two locations along its length.

In one embodiment, the angle is between 10 and 75 degrees. In still another embodiment, the overall length of the device is between 5 and 30 millimeters.

In yet another embodiment, the device further includes a sleeve disposed around the first elongated portion. In another embodiment, the distal end of the hook includes a rounded or semi-rounded tip.

In still another embodiment, the outer surface of the first elongated portion comprises a plurality of bumps disposed along its length.

In another embodiment, the cross-section of the device is at least one of square, rectangular, oval, hexagonal, octagonal, and circular.

In other embodiments, the device further includes another hook portion that includes a proximal end and a distal end, the proximal end of the hook portion being coupled to the distal end of the second elongated member.

In still other embodiments, the first elongated portion has a cross-section different from the second elongated portion, and the hook portion has a cross-section different from the second elongated portion.

In another aspect, the disclosed subject matter involves a method of performing a surgical procedure on an eye. The method includes making an incision in the cornea of an eye, and inserting into the eye through the incision, and retracting the iris with, a device as described above.

BRIEF DESCRIPTION OF THE DRAWINGS

In the drawings, like reference characters refer to the same parts throughout the different views. Also, the drawings are not necessarily drawn to scale.

FIG. 2A is an illustrative schematic diagram of the relative hooking angles, in a shallow depth eye, of a conventional iris hook (right) and a bent iris hook (left) according to one embodiment of the disclosed subject matter.

FIG. 2B is an illustrative schematic diagram of the bent iris hook of FIG. 2A.

FIG. 2C is an illustrative schematic diagram of the conventional iris hook of FIG. 2A.

FIG. 4A is an illustrative schematic diagram of the relative hooking angles, in a deep depth eye, of a conventional iris hook (right) and a bent iris hook (left) according to one embodiment of the disclosed subject matter.

FIG. 4B is an illustrative schematic diagram of the bent iris hook of FIG. 4A.

FIG. 4C is an illustrative schematic diagram of the conventional iris hook of FIG. 4A.

FIGS. 6A-6C are illustrative schematic diagrams of curved iris hooks having curves of 10, 25, and 50 degrees, respectively, according to various embodiments of the disclosed subject matter.

FIGS. 7A-7C are illustrative schematic diagrams of hook portions, according to various embodiments of the disclosed subject matter.

FIGS. 8A-8E are illustrative cross-sections of a bent iris hook, according to various embodiments of the disclosed subject matter.

FIGS. 9A-9F are illustrative schematic diagrams of hook portions with rounded or semi-rounded tips, according to various embodiments of the disclosed subject matter.

FIG. 10 is an illustrative schematic diagram of a first elongated portion of a bent iris hook that includes resistance bumps, according to one embodiment of the disclosed subject matter.

DETAILED DESCRIPTION

Figure 1:
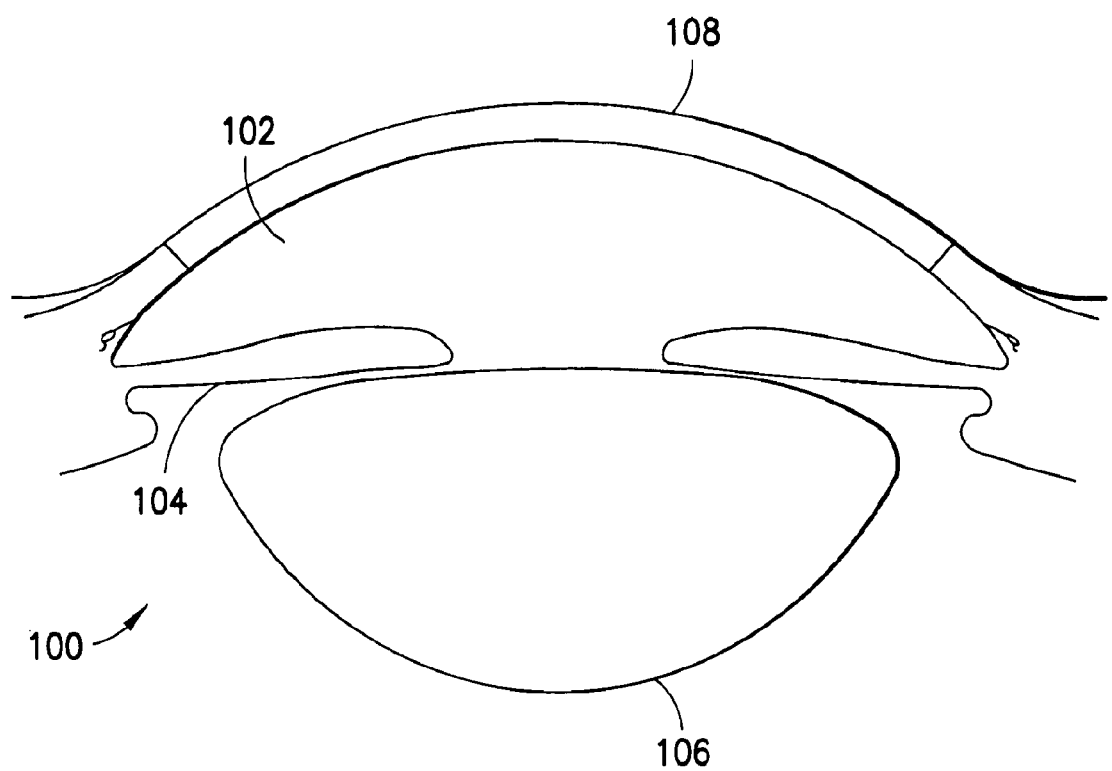
FIG. 1 is an illustrative schematic diagram of the human eye with an anterior chamber depth of 3 mm.

The disclosed subject matter provides, among other things, bent and flexible iris retraction hooks (made of nylon or any other suitable material known in the art) for use in a surgical procedure on an eye. The disclosed subject matter describes how different angles of attack designed into the flexible iris retraction hooks can reduce adverse effects caused during cataract surgery.

Studies were conducted to ascertain the effect of flexible hooks on the eye during surgery. For the purpose of such studies, a model based on the following measurements of the eye was used. The average outer diameter of the iris was 12 mm, and its circumference was 38 mm. The thickness of the iris was also quantified at 0.6 mm at the collarette (inner diameter of the iris), decreasing to 0.5 mm at the ciliary body root (outer diameter of the iris).

Since mechanical dilation occurs only if pharmacological dilation fails to provide adequate pupil size for surgery (this condition occurs most commonly in patients of advanced age), time-dependent mechanical and geometrical properties were adjusted for the age group of greater than 65 years old, wherever feasible. This model assumed the worst-case scenario of an undilated pupil with a pupil diameter of 3 mm, and a subsequent mechanical dilation to 8 mm from hook to hook, and an approximate minimum diameter of 5 mm.

It was assumed that the undisturbed iris (with a pupil size of 3 mm) was in a state of equilibrium. The model was devoid of a gravity field, so all forces result from loads applied to the model in each load case.

The load cases on the eye were defined by the geometrical requirements of a cataract operation. Since the surgeon controls the displacement rather than the force of the iris hooks on the iris, the loading conditions of this model were defined as support displacements. Since the depth of the eye (i.e., the distance between the cornea and the iris) varies greatly between patients, three different approach angles to the iris were investigated.

Angles of attack of 5°, 25°, and 45° were chosen as representative angles of attack for this model. The 5° angle represents the loading caused by a bent iris hook that accommodates for the depth of the eye, the 25° angle represents the displacement caused by conventional hook in an average eye, and the 45° angle represents the displacement caused by conventional hook in a deep eye.

For each angle of attack, a load case ("L.C.") of a single hook as well as four hooks at 90° angular spacing was defined. Since the requirements for dilation depend on the projection of the displacement onto the horizontal plane, the projection of the displacement was set at 2.5 mm for all load cases as the dilation requirement. The table below provides an overview of the six load cases defined in this model. It should be pointed out that the total displacements are not equal in these load cases. Therefore, the higher the angle of attack, the greater the overall displacement of the iris.

| Load Case Group | L.C. # | Angle of Attack | Horizontal Displacement (mm) | Vertical Displacement (mm) | Total Displacement (mm) |
|---|---|---|---|---|---|
| One Hook | 1 | 5° | 2.50 | 0.22 | 2.51 |
|  | 2 | 25° | 2.50 | 1.17 | 2.76 |
|  | 3 | 45° | 2.50 | 2.50 | 3.54 |
| Four Hooks | 4 | 5° | 2.50 | 0.22 | 2.51 |
|  | 5 | 25° | 2.50 | 1.17 | 2.76 |
|  | 6 | 45° | 2.50 | 2.50 | 3.54 |

Below is a table of the maximum tension stresses due to the previously defined loading scenarios.

| Load Case Group | L.C. # | Angle of Attack | Principal Tension (kPa) |
|---|---|---|---|
| One Hook | 1 | 5° | 337 |
|  | 2 | 25° | 503 |
|  | 3 | 45° | 845 |
| Four Hooks | 4 | 5° | 423 |
|  | 5 | 25° | 520 |
|  | 6 | 45° | 818 |

As a consequence of the model's definition, the highest deformations were caused by the 45° angle of attack. The results have shown that the tensile forces in the iris membrane are directly proportional to the hooking angle. This behavior can be deduced by application of the Pythagorean theorem. The overall displacement of the hook increases as the angle of attack is increased since the horizontal projection of the displacement is kept constant for all loading scenarios. Therefore, the tensile forces in the stretched membrane increase with a higher angle of attack since the membrane must accommodate a greater overall displacement. Consequently, a lower hooking angle that would be provided by a bent iris hook would provide a lower stress on the iris membrane than a conventional hook. It has been found that a 48% decrease of the tensile stress for a deep eye and a 36% decrease for an eye with a standard depth can be expected.

The inherently high angle of attack of straight iris hooks used in eyes with a relatively high anterior chamber depth has several adverse effects. With a straight iris hook, the iris membrane is raised during mechanical dilation. As the iris membrane is lifted, it can be easily punctured by the return end of the hook, creating additional inflammation. In addition, elevation of the iris may impede the use of surgical instruments within the anterior chamber. The use of straight hooks to support the lens capsule may also raise the capsule, potentially further destabilizing the capsule by stretching and tearing zonules.

These adverse effects are addressed by the disclosed bent iris hook. The optimal dimensions of the bend in the iris hook may vary depending on the anterior chamber depth of the eye. However, three or more sizes of bent iris hooks may well cover the range of anterior chamber depths commonly encountered in surgery.

Three anterior chamber depths are considered. Specifically, anterior chamber depths of 2 mm (shallow), 3 mm (standard), and 4 mm (deep) are considered. The bent hook geometry disclosed herein was developed by pure geometrical interpolation of the boundary of the anterior chamber. In other words, all the dimensions of the model of the eye were kept constant except the depth of the anterior chamber.

Geometric data of the eye was obtained from "Wolff's Anatomy of the Eye and Orbit", Eighth Edition, which is incorporated herein by reference. The geometry of a "standard" eye with an anterior chamber depth of 3 mm was taken from Wolff's Anatomy, and a scaled drawing of the cross-section of the eye's anterior area was drafted in AutoCAD 2006. The geometries of the shallow and deep anterior chambers were interpolated using qualitative geometric data. Specifically, the distance from the back of the cornea to the front of the lens (just behind the plane of the iris) was changed from 3 mm to 2 mm (shallow) and 4 mm (deep), respectively. The geometry of the disclosed iris hook was altered accordingly as explained in detail below.

The surgical incision for the entry of the iris hook was assumed to be located at the outer edge of the cornea, neighboring the boundary zone to the sclera. A constricted pupil with a diameter of 2.75 mm was chosen for this investigation. A maximum dilation of the iris to a diameter of 8 mm was simulated by the path of the hooks, resulting in a net horizontal projected displacement of about 2.5 mm per hook.

Referring to FIG. 1, an illustrative schematic diagram is shown of a human eye 100 with iris 104, cornea 108, lens capsule 106, and an anterior chamber 102 having a depth of 3 mm.

The purpose of using a bent hook is to minimize the angle of attack, allowing the surgeon to retract the iris 104 and/or stabilize the lens capsule 106 without inducing any unnecessary vertical displacements that may damage the iris or obstruct the surgeon.

Referring to FIG. 2A, an illustrative schematic diagram is shown of the relative hooking angles in a shallow depth eye 200 of a conventional iris hook 202 (right) and a bent iris hook 204 (left) according to one embodiment of the disclosed subject matter. FIG. 2B shows an illustrative schematic diagram of the bent iris hook 204 according to one embodiment of the disclosed subject matter, and FIG. 2C shows an illustrative schematic diagram of the conventional iris hook 202.

In the case of the shallow eye, the anterior chamber 212 has a depth of 2 mm, and the straight iris hook 202 approaches the iris 206 at a relatively low angle of 5°. This may be considered an acceptable angle of attack, since a displacement of the conventional iris hook 202 by 2.5 mm would produce a mere 0.21 mm of uplift of the iris 206. In the interest of reducing this angle to zero, a geometrical interpretation of the limiting dimensions (i.e. a bent section 208 of the bent iris hook 202 abutting the corneal incision, minimizing the angle of attack, etc.) yielded the bent iris hook 204 with an obtuse bend of 145°, a bent section 208 of 1 mm in length, and a hook return 210 of 1 mm in length. The bent iris hook 204 effectively provides an angle of attack of 0° (i.e. a horizontal retraction or stabilization force).

Figure 3A:
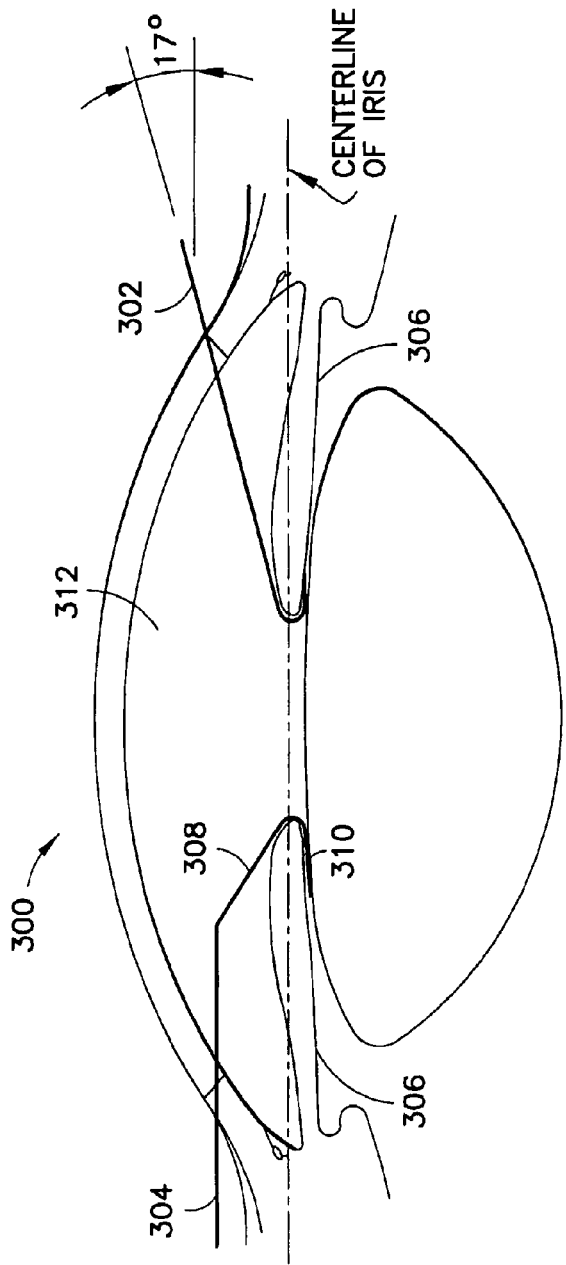
FIG. 3A is an illustrative schematic diagram of the relative hooking angles, in a standard depth eye, of a conventional iris hook (right) and a bent iris hook (left) according to one embodiment of the disclosed subject matter.
Figure 3C:
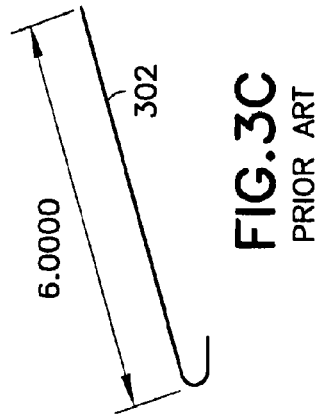
FIG. 3C is an illustrative schematic diagram of the conventional iris hook of FIG. 3A.
Figure 3B:
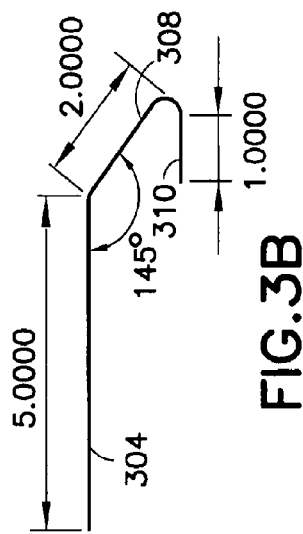
FIG. 3B is an illustrative schematic diagram of the bent iris hook of FIG. 3A.

Referring to FIG. 3A, an illustrative schematic diagram is shown of the relative hooking angles in a standard depth eye 300 of a conventional iris hook 302 (right) and a bent iris hook 304 (left) according to one embodiment of the disclosed subject matter. FIG. 3B shows an illustrative schematic diagram of the bent iris hook 304 according to one embodiment of the disclosed subject matter, and FIG. 3C shows an illustrative schematic diagram of the conventional iris hook 302.

In the case of the standard eye, the anterior chamber 312 has a depth of 3 mm, and the conventional straight hook 302 starts to reveal its weaknesses more clearly. The geometric analysis in AutoCAD yielded an angle of attack to the iris 306 of 17° resulting in an involuntary uplift of the iris 306 of 0.76 mm at a horizontal displacement of 2.5 mm. The bent iris hook 304 was developed to reduce this angle to 0°. In order to accommodate the greater anterior chamber depth (i.e., 3 mm), the bent section 308 of the iris hook 304 was increased to 2 mm in length while the bend angle remained at 145°. At this angle of attack, the danger of puncturing the iris 306 with the conventional hook 302 becomes increasingly apparent. This risk is mitigated by the geometry of the bent iris hook 304 (i.e. the lack of vertical displacement of the membrane during dilation and the horizontal orientation of the return section of the hook 310).

Referring to FIG. 4A, an illustrative schematic diagram is shown of the relative hooking angles in a deep depth eye 400 of a conventional iris hook 402 (right) and a bent iris hook 404 (left) according to one embodiment of the disclosed subject matter. FIG. 4B shows an illustrative schematic diagram of the bent iris hook 404 according to one embodiment of the disclosed subject matter, and FIG. 4C shows an illustrative schematic diagram of the conventional iris hook 402.

In the case of a deep eye, the anterior chamber 412 has a depth of 4 mm, and the objective of minimizing the angle of attack becomes increasingly more challenging. In this scenario, the conventional iris hook 402 is inclined by 29° creating as much as 1.39 mm of uplift of the iris 406 for a 2.5 mm horizontal displacement, a ratio of 1:1.8. In this case, the geometry of the cornea becomes more limiting, bounding the possible geometries of a bent iris hook 404. The bent iris hook 404 with a decreased obtuse bend of 130° and a lengthened bent section 408 of 3 mm provides an optimal fit in the geometric analysis. Unlike the previous scenarios, it is not feasible to reduce the angle of attack to zero, as this would have required an even more acute bend angle (i.e., creating a further bending moment in the bent section 408 of the bent iris hook 404). In this case, the angle of attack was reduced to 4°, reducing the uplift of the iris 406 from 1.39 mm to 0.17 mm with a horizontal displacement of 2.5 mm.

Figure 4D:
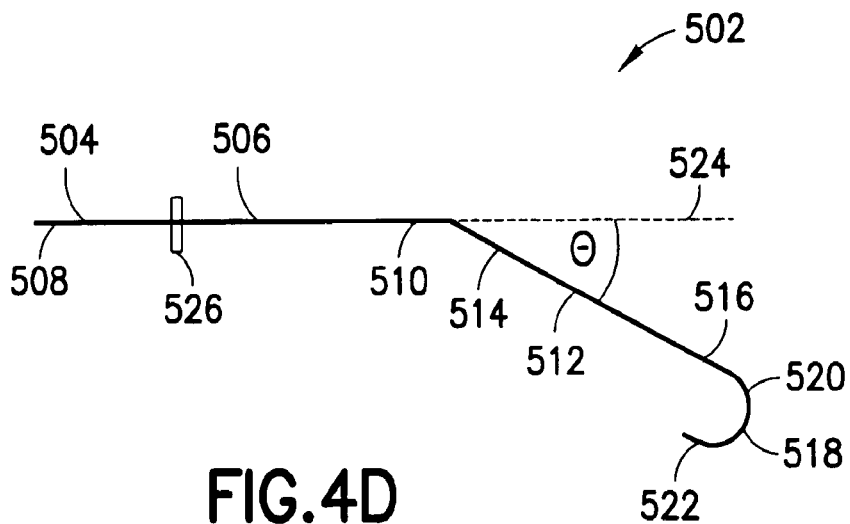
FIG. 4D is an illustrative schematic diagram of a bent iris hook, according to one embodiment of the disclosed subject matter.

Referring to FIG. 4D, in one embodiment, an illustrative schematic diagram of a bent iris hook 502 is shown. The bent iris hook 502 includes an elongated member 504. The elongated member 504 includes a first elongated portion 506, a second elongated portion 512, and a hook portion 518.

The first elongated portion 506 includes a proximal end 508 and a distal end 510. The second elongated portion 512 includes a proximal end 514 and a distal end 516. The proximal end 514 of the second elongated portion 512 is coupled to the distal end 510 of the first elongated portion 506. The second elongated portion 512 extends from the first elongated portion 506 at an angle $\Theta$ to the longitudinal axis 524 of the first elongated portion 506. The hook portion 518 includes a proximal end 520 and a distal end 522. The proximal end 520 of the hook portion 518 is coupled to the distal end 516 of the second elongated member 512. The point at which the second elongated portion 512 bends away at angle $\Theta$ from the longitudinal axis 524 of the first elongated portion 506 can occur at any location along the length of the elongated member 504.

In various embodiments, the overall length of iris hook 502 is between 5 and 30 millimeters. In another embodiment, a sleeve 526 is disposed around the first elongated portion 506 and held in place via a friction fit. The sleeve 526 can be manually positioned along the length of the iris hook 502 to hinder the iris hook 502 from being inadvertently drawn into the incision due to tension from the iris. In one embodiment, the sleeve is made of silicone.

Figure 5A:
FIGS. 5A-5C are illustrative schematic diagrams of bent iris hooks having bends of 10, 25, and 50 degrees, respectively, according to various embodiments of the disclosed subject matter.
Figure 5B:
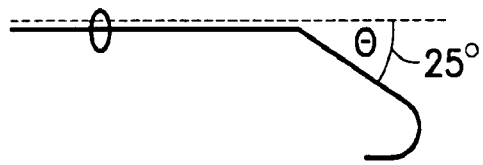
Figure 5C:
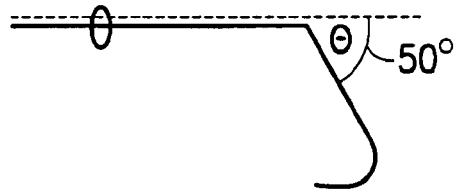

Referring to FIGS. 5A-5C, illustrative schematic diagrams of various embodiments of bent iris hooks are shown. In these embodiments, the bent portion is straight and bends away from the longitudinal axis (indicated by the dashed line) at an angle $\Theta$ of 10, 25, and 50 degrees, respectively. In other embodiments, the angle $\Theta$ can range from 10 to 75 degrees.

Referring to FIGS. 6A-6C, illustrative schematic diagrams of various embodiments of curved iris hooks are shown. In these embodiments, a portion of the bent iris hook curves away from the longitudinal axis (indicated by the dashed line) at an angle $\Theta$ of 10, 25, and 50 degrees, respectively. In other embodiments, the angle $\Theta$ can range from 10 to 75 degrees. In this embodiment, the angle $\Theta$ is determined by the angle between the longitudinal axis and a line (indicated by the dot-dash line) that extends through the point of the first bend (i.e., the point where the hook begins to curve away from the longitudinal axis) and the point of the second bend (i.e., the point where the hook begins to curve).

Referring to FIGS. 7A-7C, illustrative schematic diagrams of hook portions are shown. In various embodiments, the hook portion can be bent in an acute angle (FIG. 7A), curved like a circle (FIG. 7B), or bent at two locations along the length of the hook portion (FIG. 7C). The size of the hook portion is determined by the surgical need.

Referring to FIGS. 8A-8E, illustrative cross-sections of a bent iris hook are shown. In various embodiments, the bent iris hook can have a cross-section that is circular (FIG. 8A), rectangular (FIG. 8B), oval (FIG. 8C), square (FIG. 8D), octagonal (FIG. 8E), or hexagonal, or any other shape that serves a clinical need. Further, in one embodiment, the first elongated portion 506 has a cross-section different from the second elongated portion 512. In another embodiment, the hook portion 518 has a cross-section different from the first and second elongated portions 506, 512. For example, the cross-section of the hook portion 518 which contacts the iris can be rounded (e.g., circular or oval) in order to create less irritation of the iris, and the first and second elongated portions 506, 512 can be square or rectangular in order to improve gripping the iris hook 502 securely and to increase the iris hook's resistance to bending.

Referring to FIGS. 9A-9F, according to various embodiments, illustrative schematic diagrams of hook portions having rounded tips 902, 904, 906, and semi-rounded tips 908, 910, 912, respectively, are shown. The rounded or semi-rounded tip configuration helps prevent the end of the bent iris hook from tearing or puncturing the iris.

The tips 902, 904, 906, 908, 910, 912 (which contact the iris during surgery) are rounded or semi-rounded rather than sharp in order to better distribute the forces exerted on the iris regardless of the angle of contact between the tip and the iris. Otherwise, if an iris hook with a sharp tip is used, at certain angles of contact with the iris, the concentration of forces is so high that the iris hook causes irritation to the underside of the iris, which can create inflammation. In still other embodiments, the rounded or semi-rounded tip is polished or coated by any material that is eye safe and will make the tip smoother, such as silicone or Teflon, for example.

Referring to FIG. 10, in another embodiment, an illustrative schematic diagram of a first elongated portion of a bent iris hook that includes a plurality of resistance bumps 1002 is shown.

With conventional iris hooks, the handle is shaped such that when the pupil constricts, the sleeve 526 (FIG. 5A) may undesirably slide along the iris hook and thereby allow the pupil to constrict further.

In one embodiment, to prevent the sleeve 526 from undesirably sliding along the elongated member, the first elongated portion (or the first and second elongated portions) of the bent iris hook include resistance bumps 1002 that increase the resistance to movement of the hook within the incision and the silicone sleeve along the bent iris hook. This prevents the bent iris hook from being drawn into the incision due to tension from the iris. In another embodiment, a bent iris hook including the resistance bumps 1002 without the sleeve 526 may be used if the resistance of the incision is sufficient to prevent the bent iris hook from being drawn through the incision and further into the anterior chamber.

Figure 11:
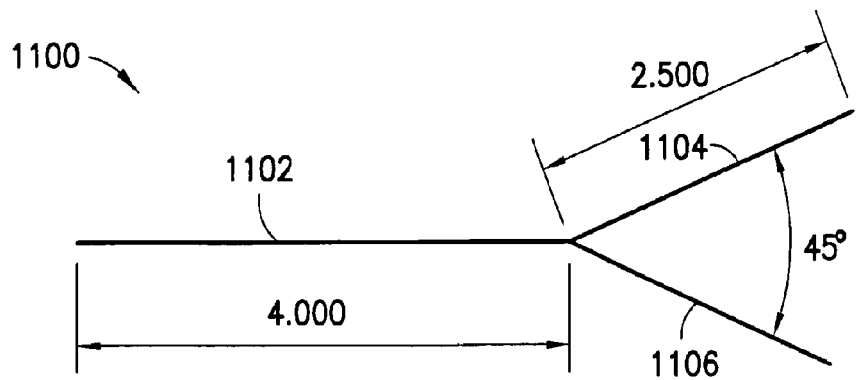
FIG. 11 is an illustrative plan view of a forked bent iris retraction hook according to one embodiment of the disclosed subject matter.
Figure 12:
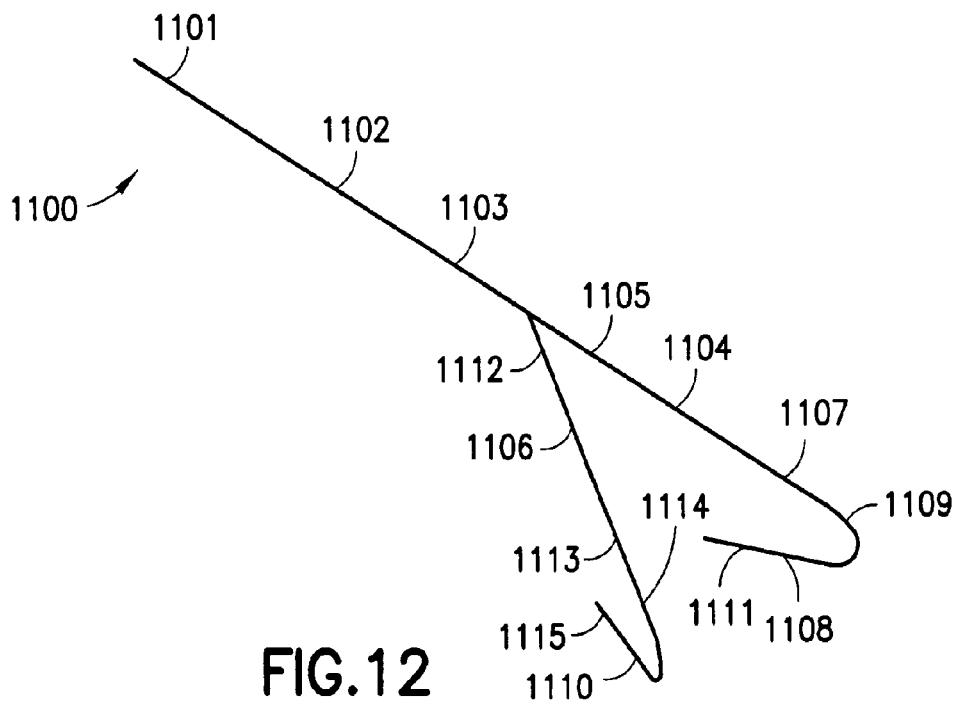
FIG. 12 is an illustrative elevation view of a forked bent iris retraction hook according to one embodiment of the disclosed subject matter.
Figure 13:
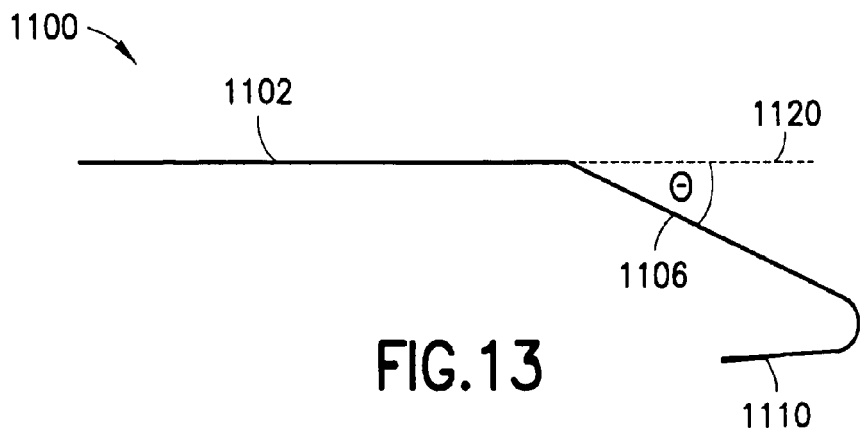
FIG. 13 is an illustrative orthographic view of a forked bent iris retraction hook according to one embodiment of the disclosed subject matter.

Referring to FIGS. 11-13, in one embodiment, a forked bent iris retraction hook 1100 is shown. The forked bent iris retraction hook 1100 includes a first elongated member portion 1102, a second elongated member portion 1104, a third elongated member portion 1106, a first hook portion 1108, and a second hook portion 1110.

The first elongated portion 1102 includes a proximal end 1101 and a distal end 1103. The second elongated portion 1104 includes a proximal end 1105 and a distal end 1107. The third elongated portion 1106 includes a proximal end 1112 and a distal end 1113. The proximal end 1105 of the second elongated portion 1104 is coupled to the distal end 1103 of the first elongated portion 1102. The proximal end 1112 of the third elongated portion 1106 is also coupled to the distal end 1103 of the first elongated portion 1102.

The second elongated portion 1104 extends from the first elongated portion 1102 at an angle $\Theta$ to the longitudinal axis 1120 of the first elongated portion 1102. The third elongated portion 1106 also extends from the first elongated portion 1102 at an angle $\Theta$ to the longitudinal axis 1120 of the first elongated portion 1102.

The first hook portion 1108 includes a proximal end 1109 and a distal end 1111. The proximal end 1109 of the first hook portion 1108 is coupled to the distal end 1107 of the second elongated member 1104. The second hook portion 1110 includes a proximal end 1114 and a distal end 1115. The proximal end 1110 of the second hook portion 1110 is coupled to the distal end 1113 of the third elongated member 1106.

The forked bent iris retraction hook 1100 reduces the compressive force at the contact point between the iris/lens capsule and the hook portions 1108, 1110. The forked bent iris retraction hook 1100 also provides a more circular dilation due to the increased number of abutment points. If four hooks are used to dilate an iris, then the maximum dilation diameter is reached at eight points, instead of four, creating a more well-rounded work area for surgery. Like the previous model, the forked bent iris retraction hook 1100 was designed on a purely geometric basis, aiming to reduce the overall tensile stress state of the dilated iris and providing more effective dilation by effectively increasing the number of hooks used in the dilation.

It is apparent that a bent iris hook as described herein would provide more desirable displacements on the iris and lens capsule during surgery. This greatly reduces unwanted uplift caused by high angles of attack, greatly reducing the risk of destabilizing lens capsules and puncturing the iris membrane. Of course, the forces that would develop in such a bent iris hook must be taken into account. It appears that a more rigid material than the nylon (6-0 nylon) currently used for flexible hooks would be required to resist the bending moment caused by the eccentricity of the application and reaction of the pulling force. In this case, the disclosed bent iris hooks can be fabricated from nylon of a greater cross-section (surgical grade 5-0 or 4-0), or an alternative material such as polymethylmethacrylate, for example.

As shown above, there is a significant difference in the stress state and the deformation of the structure of the eye with respect to the type of iris hook used in surgery. Using a conventional straight iris hook results in a high angle of incidence, while using the bent iris hook disclosed herein results in a low angle of incidence.

As seen in the purely geometrical treatment of the hooking scenarios, the bent iris hook described herein provides a much lower angle of attack and, therefore, also greatly reduces the chance of piercing the iris membrane as it is being dilated. The prevention or at least the reduction of the risk of occurrence of this complication is very favorable in view of the bent iris hook design described herein. The disclosed bent iris hook also lifts the iris less than a conventional straight iris hook. This feature allows easy manipulation of surgical instruments with the anterior chamber of the eye during surgery.

Further, the forked bent iris hook described herein provides the greatest net improvement of the stress state of the iris. This design not only reduces the maximum tensile and compressive forces responsible for damage to the iris membrane, it also results in a rounder dilation area, providing better access to the surgeon.

Variations, modifications, and other implementations of what is described herein may occur to those of ordinary skill in the art without departing from the spirit and scope of the disclosed subject matter. Accordingly, the disclosed subject matter is not to be defined only by the preceding illustrative description.

What is claimed is:

1. A device for use in a surgical procedure on an eye, comprising:
   a flexible elongated member comprising:
      a first elongated portion comprising a proximal end and a distal end;
      a second elongated portion comprising a proximal end and a distal end, the proximal end of the second elongated portion extending from the distal end of the first elongated portion so that the first elongated portion and the second elongated portion form an obtuse angle at the distal end of the first elongated portion, the obtuse angle opening in a direction facing away from a first side of the second elongated portion; and
      a hook portion comprising a proximal end and a distal end, the proximal end of the hook portion extending from the distal end of the second elongated portion, the hook portion forming an acute angle which opens in the direction facing away from the first side of the second elongated portion,
   wherein the obtuse angle is between 105 and 170 degrees,
   the device is adapted to perform surgical retraction of the iris of the eye, and
   the obtuse angle between the first elongated portion and the second elongated portion is located inside the eye when the hook portion is retracting the iris.

2. The device according to claim 1, wherein the second elongated portion is straight.

3. The device according to claim 1, wherein the second elongated portion is curved.

4. The device according to claim 1, wherein the overall length of the device is between 5 and 30 millimeters.

5. The device according to claim 1, wherein the hook is curved.

6. The device according to claim 1, wherein the hook is bent at an acute angle.

7. The device according to claim 1, wherein the hook is bent at two locations along its length.

8. The device according to claim 1, further comprising a sleeve disposed around the first elongated portion.

9. The device according to claim 1, wherein the distal end of the hook comprises a rounded or semi-rounded tip.

10. The device according to claim 1, wherein an outer surface of the first elongated portion comprises a plurality of bumps disposed along its length.

11. The device according to claim 1, wherein the cross-section of the device is at least one of square, rectangular, oval, hexagonal, octagonal, and circular.

12. The device according to claim 1 further comprising a second hook portion comprising a proximal end and a distal end, the proximal end of the second hook portion extending from the distal end of the second elongated portion.

13. The device of claim 1, wherein the first elongated portion has a cross-section different from the second elongated portion.

14. The device of claim 1, wherein the hook portion has a cross-section different from the second elongated portion.

15. A method of performing a surgical procedure on an eye comprising:
   making an incision in the cornea of an eye; and
   inserting into the eye through the incision, and retracting the iris with, a device according to claim 1.

16. The device of claim 1, wherein the device is adapted to perform surgical retraction of a structure of the eye.

17. The device of claim 1, wherein the elongated member is formed of a non-metallic material.

18. The device of claim 1, wherein the elongated member is formed of nylon.

19. The device of claim 1, wherein the elongated member is formed of polymethylmethacrylate.

20. The device of claim 1, wherein the elongated member has a rigidity less than or equal to that of surgical grade 5-0 nylon.

21. The device of claim 1, wherein the elongated member has a rigidity less than or equal to that of surgical grade 4-0 nylon.

22. The device of claim 1, wherein a ratio of a length of the hook portion relative to a length of the second elongated portion is between about 1:1 and about 1:3.

23. The device of claim 1, wherein a ratio of a length of the second elongated portion relative to a length of the first elongated portion is between about 1:5 and about 3:5.

* * * * *